United States Patent [19]
Becker et al.

[11] Patent Number: 5,895,423
[45] Date of Patent: Apr. 20, 1999

[54] ATTACHABLE TWO-CHAMBER BREAST PROSTHESIS

[75] Inventors: Anne Roesler Becker, Marietta; Michael Anthony DiMarco, Atlanta, both of Ga.; Diane Taryn-Leigh Hodgkins, Bellingham, Wash.; Louis F. Malice, Jr., Marietta, Ga.

[73] Assignee: Coloplast Corporation, Marietta, Ga.

[21] Appl. No.: 08/803,201

[22] Filed: Feb. 21, 1997

Related U.S. Application Data

[60] Provisional application No. 60/012,216, Feb. 23, 1996.

[51] Int. Cl.$^6$ .................................................. A61F 2/52
[52] U.S. Cl. ........................... 623/7; 623/8; 623/12; 623/901
[58] Field of Search .................... 623/7, 8, 12, 901

[56] References Cited

U.S. PATENT DOCUMENTS

| | | | |
|---|---|---|---|
| 4,172,298 | 10/1979 | Rechenberg | 3/36 |
| 4,247,351 | 1/1981 | Rechenberg | 156/221 |
| 4,950,291 | 8/1990 | Mulligan | 623/8 |
| 5,071,433 | 12/1991 | Næstoft et al. | 623/7 |
| 5,352,307 | 10/1994 | Wild | 156/66 |

*Primary Examiner*—Edward J. Cain
*Attorney, Agent, or Firm*—Jones & Askew, LLP

[57] ABSTRACT

An attachable two-chamber breast prosthesis includes two volumes of silicone materials that have different degrees of softness. The prosthesis includes three pieces of polyurethane film (a front film, a middle film, and a rear film) that form a front chamber and rear chamber. The periphery of the front chamber is smaller than the periphery of the rear chamber. The rear chamber, which contains the firmer silicone material, extends to the peripheral edge of the prosthesis. The front chamber, which contains the softer silicone material, does not extend all the way to the peripheral edge along the upper region of the prosthesis. By increasing the thickness of the rear chamber along a boomerang-shaped region defined by the peripheries of the front and rear chambers, the firmer silicone material in the rear chamber provides the prosthesis with proper support and reduces the tendency of the prosthesis to pull away from the skin along the top edge of the prosthesis.

25 Claims, 4 Drawing Sheets

ATTACHABLE TWO-CHAMBER BREAST PROSTHESIS

STATEMENT REGARDING RELATED APPLICATION

This application claims the benefit of U.S. Provisional Application No. 60/012,216, entitled "Attachable Two-Chamber Breast Prosthesis," filed Feb. 23, 1996.

BACKGROUND OF THE INVENTION

It is an unfortunate fact that many women contract breast cancer and must have the affected breast removed. After removal of one or both breasts, most mastectomy patients in today's society seek a prosthetic replacement to feel whole, and present a normal appearance beneath clothing. Another goal of breast prostheses is to reduce stress on the spine by maintaining the body's natural balance. Early fabric prostheses were never very satisfactory, and surgically implanted prostheses are expensive and involve health risks. Therefore, external silicone breast prostheses have become extremely popular with mastectomy patients.

The first external silicone breast prostheses included a single volume of a two-component cross-linked silicone material contained within a cavity formed by two pieces of polyurethane film. The silicone material is cured in a mold that determines the shape of the prosthesis. Such prostheses were designed to be worn inside a brassiere. An example of such a prosthesis and a mold are described in U.S. Pat. Nos. 4,172,298 and 4,247,351 to Rechenberg.

Eventually, prosthesis designers determined that certain advantages could be obtained by forming a prosthesis from two volumes of silicone materials that have different degrees of softness. Such prostheses include three pieces of polyurethane film, which are welded together along a common peripheral edge to form front and rear chambers. In some products, the firmer silicone material is in the front chamber. In others, the firmer silicone material is in the rear chamber.

U.S. Pat. No. 4,950,291 to Mulligan describes a two-chamber prosthesis in which the front chamber is relatively thin. The silicone material in the larger rear chamber, which is placed next to the chest wall, is softer than that in the front chamber. The softer silicone material conforms to the shape of the chest wall and moves with the body, thereby providing a natural appearance. The softer silicone material helps redistribute the weight of the prosthesis across and against the chest wall and away from the brassiere shoulder strap, which reduces stress on the shoulder. The firmer silicone material in the front chamber supports the soft rear chamber, prevents the prosthesis from collapsing, and gives shape to the product.

As mentioned above, other two-chamber prostheses place the firmer silicone material in the rear chamber. An example of a two-chamber prosthesis of this type is sold by the assignee of the present invention under the trademark "DELTA PERSONALLY." In this prosthesis, the rear chamber, which contains the firmer silicone material, is relatively thin. The larger front chamber contains the softer silicone material. This configuration is advantageous because the firmer rear chamber simulates the pectoralis chest muscles while the softer front chamber moves like a natural breast. This prosthesis provides a significant natural drape with softness to fill and mold to a brassiere cup completely and naturally. The overall softness of the prosthesis helps the prosthesis mold to the chest wall and helps redistribute the weight of the prosthesis across and against the chest wall and away from the brassiere shoulder strap.

Subsequent developments led to the introduction of attachable prostheses, which could be attached to the skin of the wearer. Like the earlier silicone prostheses, the attachable products included a single volume of a two-component cross-linked silicone material contained within a cavity formed by two pieces of polyurethane film. The prosthesis is held in place on the wearer's chest by a skin support or fastening slab, which has a skin-friendly adhesive on one side and an attachment members on the other side. The prosthesis is attached to the skin support by complementary attachment members. U.S. Pat. No. 5,071,433 to Naestoft et al. and U.S. Pat. No. 5,352,307 to Wild describe attachable prostheses that employ hook-and-loop fasteners, where the hook material is on the prosthesis and the loop material forms one side of the skin support.

Although it may appear to be a simple matter to combine the attachment members of the Naestoft patent with the two-chamber prostheses described above, the simple combination of these features leads to unsatisfactory results. In the case of the soft back two-chamber prosthesis, the back chamber is too soft to support the weight of the prosthesis. In the case of the soft front two-chamber prosthesis, the soft front tends to droop under the weight of the prosthesis and cause the top portion of the prosthesis to pull away from the wearer' skin. Although this may be remedied to some degree by moving the attachment members up along the top edge of the prosthesis, this results in positioning of the skin support that is unacceptable for two reasons. First, the skin support must be positioned so close to the edge of prosthesis that it may be visible around the edges of the prosthesis. Second, this configuration tends to suspend most of the weight of the prosthesis from the top of the skin support, which tends to peel the skin support away from the wearer's skin.

Therefore, there is a need in the art for an attachable, two-chamber prosthesis. An attachable two-chamber prosthesis should provide an acceptable fit and transition to the wearer's chest. Furthermore, an attachable two-chamber prostheses must allow the skin support to be adequately concealed beneath the prostheses and minimize the tendency to peel the skin support away from the wearer's skin.

SUMMARY OF THE INVENTION

The present invention satisfies the above-described need by providing an attachable two-chamber breast prosthesis in which the periphery of the front chamber is smaller than the periphery of the rear chamber. The prosthesis includes three pieces of polyurethane film that are joined together to form a front chamber and rear chamber. The periphery of the rear chamber extends to the peripheral edge of the prosthesis. The periphery of the front chamber is smaller than the periphery of the rear chamber.

Generally described, the present invention provides a breast prosthesis that includes a front portion and a rear portion. The front portion is enclosed between a first film and a second film and has a first periphery. The rear portion is enclosed between the second film and a third film and has a second periphery. The first periphery is smaller than the second periphery.

More particularly described, the front and rear portions of the prosthesis include gel-like materials, such as two-component cross-linked silicone materials. The gel-like material in the front portion is softer than the gel-like material in the rear portion. The first, second, and third films comprise polyurethane.

In another aspect, the present invention provides an attachable two-chamber breast prosthesis. The prosthesis includes a front chamber formed by a first film and a second film. The front chamber is filled with a first gel-like material. The prosthesis also includes a rear chamber formed by the second film and a third film. The rear chamber is filled with a second gel-like material. An upper region is formed by joining the first film and the second film along a two-dimensional area. The joining of the first and second films to form the upper region results in the periphery of the front chamber being smaller than the periphery of the rear chamber. Attachment members are affixed to the exterior of the rear chamber.

In yet another aspect. the present invention provides a method for manufacturing a breast prosthesis. The method includes joining a two-dimensional area of a first film and a second film to form an upper region of the prosthesis. The first film, the second film, and a third film are joined along a peripheral edge to form a first chamber between the first film and the second film and a second chamber between the second film and the third film. The first chamber has a periphery that is smaller than the periphery of the second chamber. The joined plastic films are placed in a mold, which defines the shape of the prosthesis. First and second gel-like materials are introduced into the first and second chambers, respectively. and the gel-like materials are cured.

In view of the foregoing, it will be appreciated that the present invention and its various embodiments will be more fully understood from the detailed description below. when read in connection with the accompanying drawings, and in view of the appended claims.

DETAILED DESCRIPTION

The present invention will now be described with reference to the drawings, in which like numerals represent like elements throughout the several views. An attachable two-chamber breast prosthesis constructed in accordance with the present invention provides an acceptable fit and transition to the wearer's chest while allowing the skin support to be adequately concealed beneath the prostheses and minimizing the tendency to peel the skin support away from the wearer's skin. However, prior to describing an exemplary attachable two-chamber breast prosthesis, it is helpful to briefly describe the construction of a prior art two-chamber prosthesis.

Figure 1:
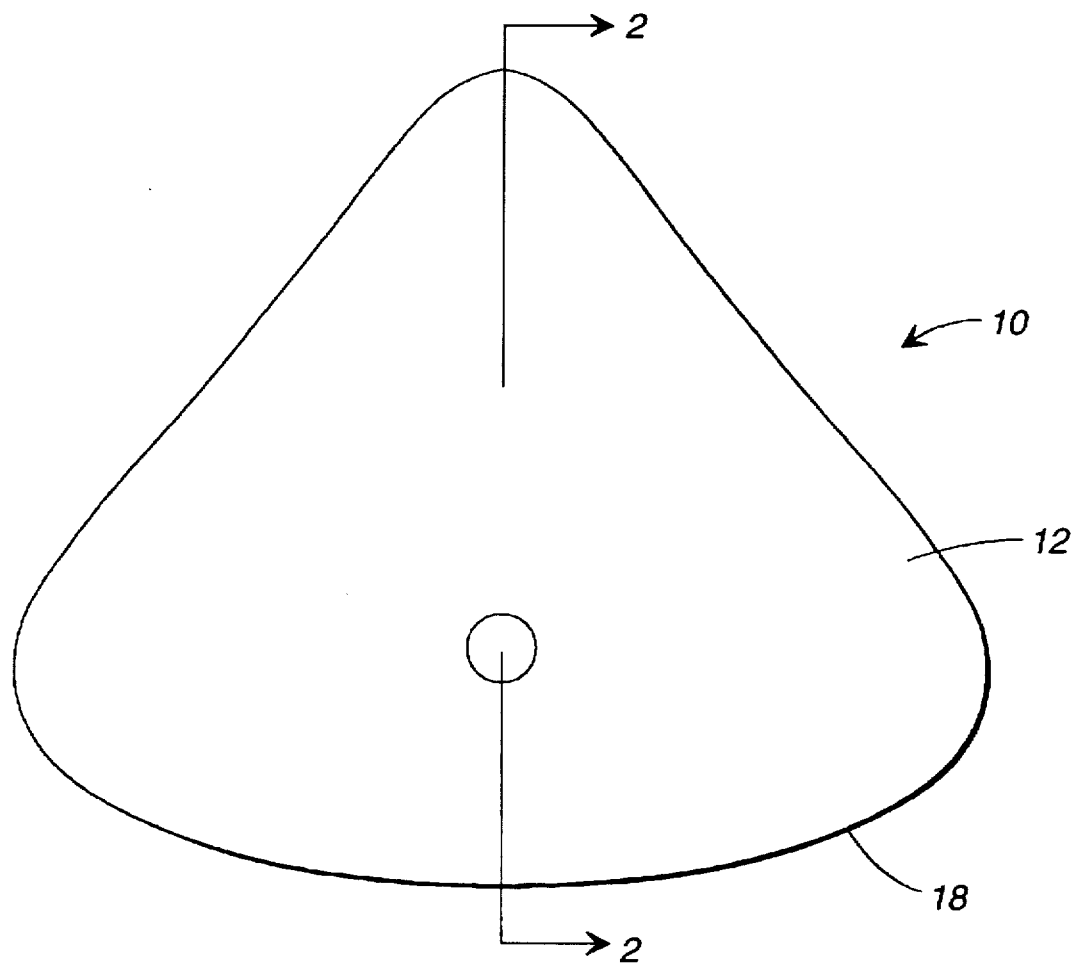
FIG. 1 is a top view of a prior art non-attachable two-chamber breast prosthesis.
Figure 2:
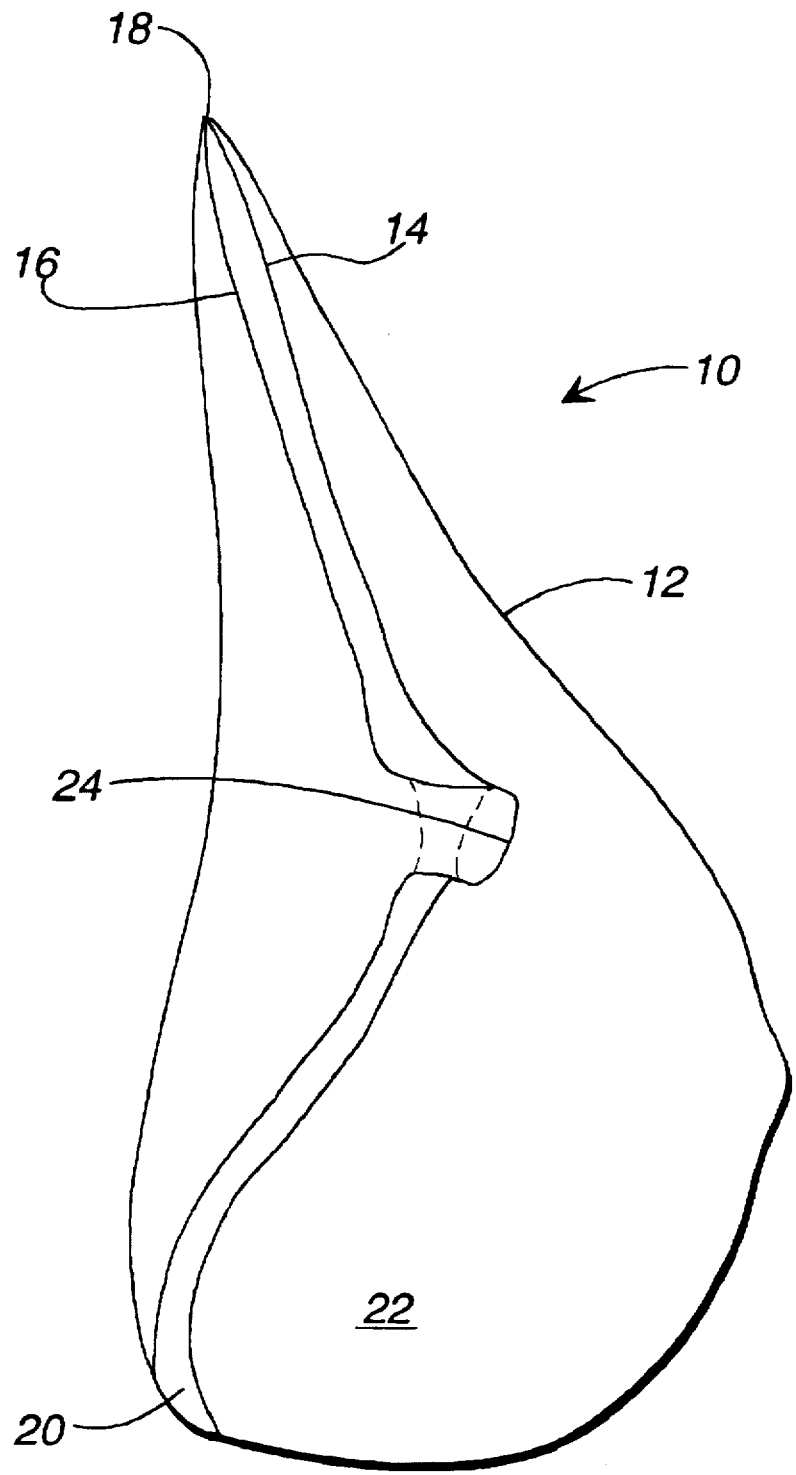
FIG. 2 is a cross-sectional view of the prior art two-chamber prosthesis of FIG. 1 taken along the line 2—2 of FIG. 1.

FIGS. 1 and 2 illustrate a prior art, non-attachable, two-chamber breast prosthesis 10 sold by the assignee of the present invention under the trademark "DELTA PERSONALLY." The prior art prosthesis 10 includes two volumes of silicone rubber materials that have different degrees of softness. The prior art prosthesis 10 includes three pieces of polyurethane film (front film 12, middle film 14, and rear film 16), which are welded together along a common peripheral edge 18 to form a front chamber 22 and a rear chamber 20. In the prior art prosthesis 10, the silicone material in the front chamber 22 is softer than the silicone material in the rear chamber 20. As mentioned above, this configuration is advantageous because the firmer rear chamber simulates the pectoralis chest muscles and supports the prosthesis while the soft front chamber moves like a natural breast.

As illustrated in the cross section of FIG. 2, the rear chamber 20 is relatively thin. At the approximate center of the rear of the prior art prosthesis 10, there is an indentation 24, which is formed by a protrusion on the mold during the oven curing process. Prior to injecting the silicone material into the front and rear chambers, the middle film 14 and rear film 16 are welded together at the point of the indentation 24 in order to ensure that there is sufficient film to film adhesion at that point. The protrusion and the weld, which result in the indentation 24, ensure that the firmer silicone material in the thin rear chamber 20 is properly distributed during the curing process.

Figure 3:
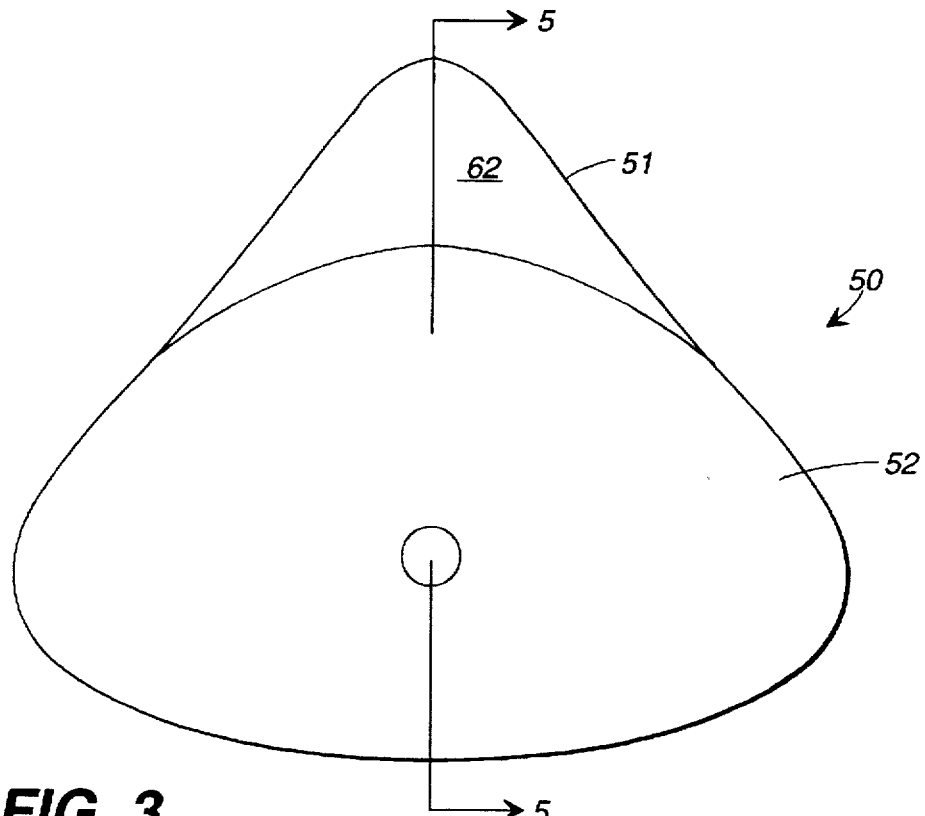
FIG. 3 is a top view of an attachable two-chamber breast prosthesis constructed according to the present invention.
Figure 4:
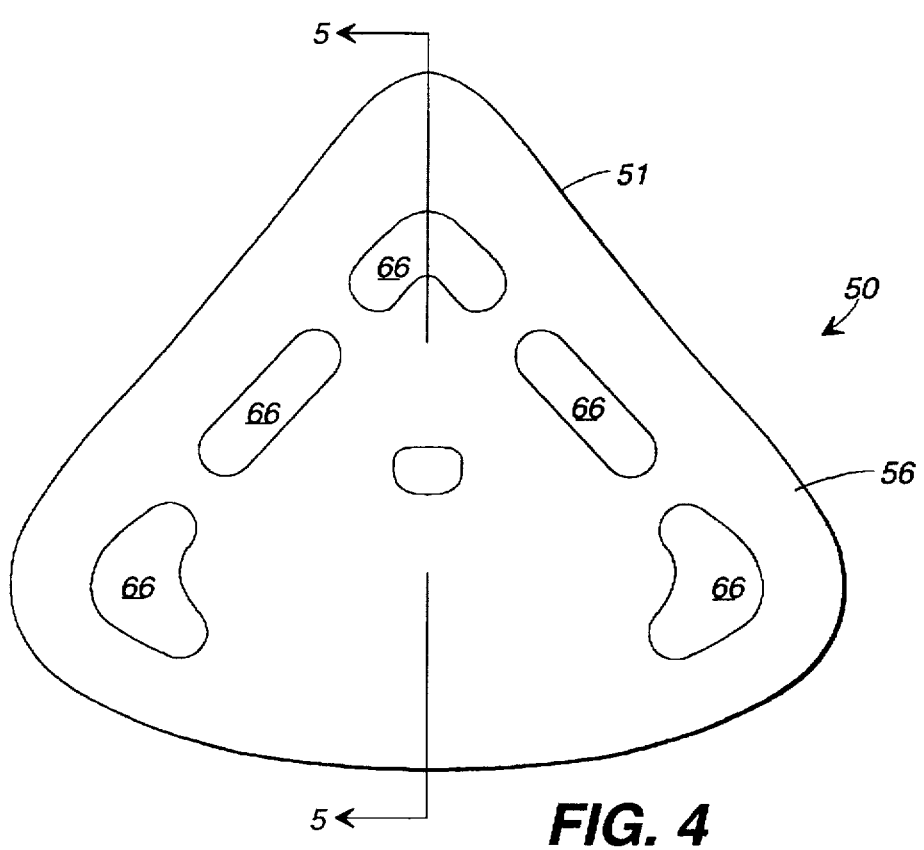
FIG. 4 is a rear view of the attachable two-chamber breast prosthesis of FIG. 3.
Figure 5:
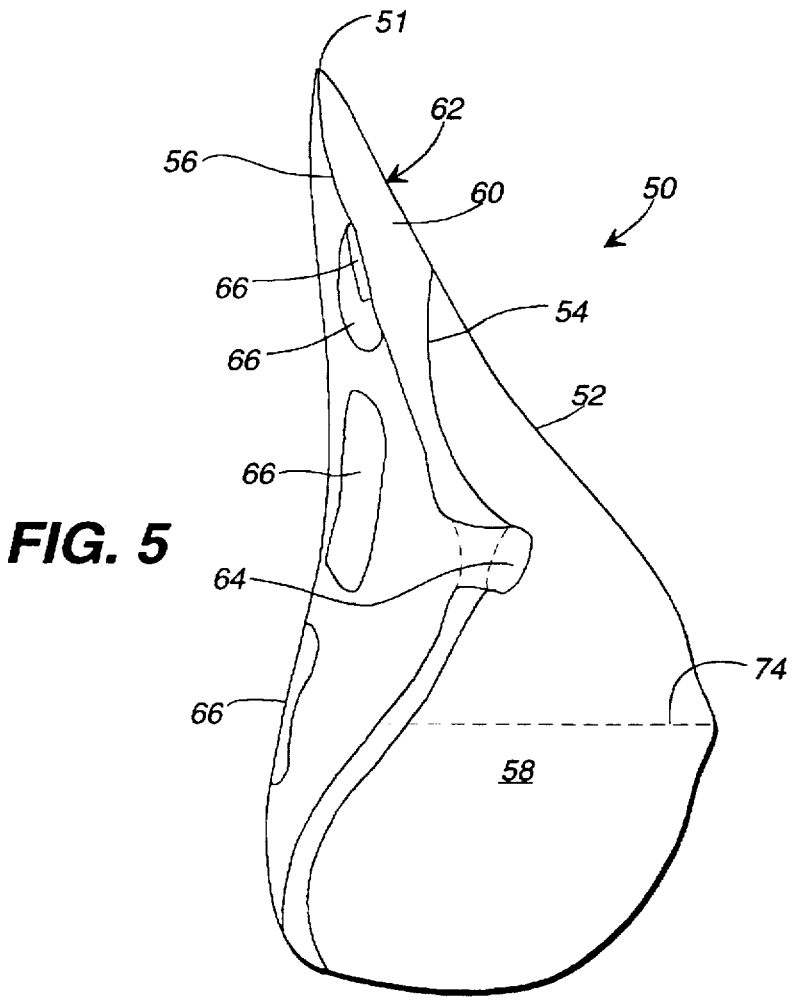
FIG. 5 is a cross-sectional view of the attachable two-chamber prosthesis of FIGS. 3 and 4 taken along the line 5—5 of FIGS. 3 and 4.

Referring now to FIGS. 3-5. an exemplary attachable two-chamber breast prosthesis 50 will be described. Generally described, the attachable two-chamber prosthesis 50 is a shell shaped silicone pad consisting of two volumes of silicone materials (or other suitable gel-like materials) within a film assembly. The prosthesis 50 approximates the shape of a normal breast, forms a generally concave rear cavity, and tapers to form a peripheral edge 51.

Like the prior art prosthesis 10 (FIGS. 1 and 2), the attachable two-chamber prosthesis 50 includes two volumes of silicone rubber materials that have different degrees of softness. The attachable two-chamber prosthesis 50 includes three pieces of polyurethane film (front film 52, middle film 54, and rear film 56) that form a front chamber 58 and rear chamber 60. However, unlike the prior art prosthesis 10, the periphery of the front chamber 58 is smaller than the periphery of the rear chamber 60. As illustrated in FIGS. 3 and 5, the rear chamber 60, which contains the firmer silicone material, extends to the peripheral edge 51 of the attachable two-chamber prosthesis 50. However, the front chamber 58, which contains the softer silicone material, does not extend all the way to the top edge of the attachable two-chamber prosthesis 50. By increasing the thickness of the rear chamber 60 along a boomerang-shaped upper region 62 of the attachable two-chamber prosthesis 50, the firmer silicone material in the rear chamber provides the prosthesis with proper support and reduces the tendency of the prosthesis to pull away from the skin along the top edge of the prosthesis.

Like the prior art prosthesis 10 (FIG. 1), the attachable two-chamber prosthesis 50 also includes an indentation 64 at the approximate center of the rear surface. The indentation 64 is formed by a protrusion on the mold during the oven curing process. Prior to injecting the silicone material into the front and rear chambers, the middle film 54 and rear film 56 are welded together at the point of the indentation 64 in order to ensure that there is film to film adhesion at that point. The protrusion and the weld, which result in the indentation 64, ensure that the firmer silicone material in the thin rear chamber 60 is properly distributed during the curing process.

The attachable two-chamber prosthesis 50 also includes a plurality of attachment members 66, which are affixed to the exterior side of the rear film 56 during the curing process.

Figure 6:
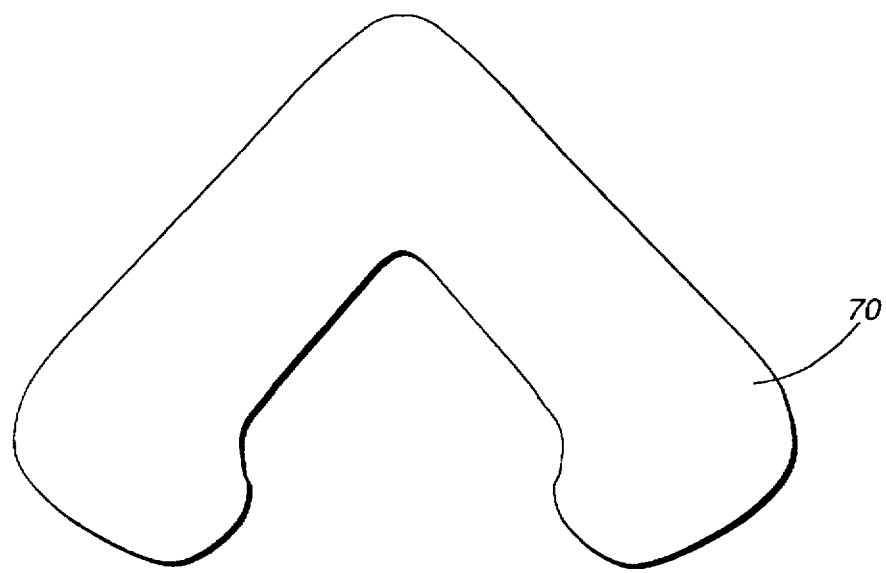
FIG. 6 is a top view of a skin support suitable for attaching the attachable two-chamber breast prosthesis of FIG. 3 to the skin of the wearer.

The attachment members 66 are used to attach the prosthesis 50 to a skin support 70 (FIG. 6), which is attached to the skin of a wearer. One side of the skin support 70 includes a skin-friendly adhesive. The other side includes one part of a two-part complementary fastening system, such as a hook and loop type fastener. The attachment members 66 provide the second part of the two part complementary fastening system. Preferably, the skin support 70 is first attached to the wearer's skin using a skin friendly adhesive. The prosthesis 50 is then attached to the skin support 70 using by means of the two-part complementary fastening system. The attachment members 66 consist of the hook portion of the two-part complementary fastening system and the outer surface of the skin support provides the complementary loop portion. An attachable one-chamber prosthesis using hook-and-loop fasteners is described in U.S. Pat. No. 5,071,433 to Naestoft et al., which is incorporated herein by reference. A method of attaching attachment members to a prosthesis is described in U.S. Pat. No. 5,352,307 to Wild, which is incorporated herein by reference.

The boomerang shaped upper region 62 will now be described in additional detail. The present inventors wanted to keep the height of the boomerang-shaped upper region 62 as small as possible without compromising the prosthesis' fit. The present inventors determined that in order to provide the best fit, the softer silicone material in the front chamber 58 should not extend above the approximate center of the top attachment member 66. The position of the attachment members 66 is determined in part by the position of the skin support 70 (FIG. 6) relative to the peripheral edge 51 of the prosthesis. Those skilled in the art will understand that the skin support should be positioned well within the peripheral edge of the prosthesis in order to ensure that the skin support is not visible. Therefore, the position of the attachment members is determined in order to ensure that the skin support is concealed, and the top edge of the front chamber 58 is located spaced down from the top of the top attachment member, preferably at or below the approximate center of the top attachment member. In an exemplary attachable two-chamber prosthesis 50 the height of the boomerang-shaped upper region is approximately 25% of the height of the prosthesis.

The exemplary attachable two-chamber prosthesis 50 may be manufactured in the following manner. Generally described, the process requires joining three sheets of polyurethane film to form the chambers that will contain the silicone material. After the bag is formed, it is placed in a mold and each chamber is filled with two two-component cross-linking silicone materials. The silicone materials are then cured by heating the mold.

The three sheets of polyurethane film are joined in the following manner. First, two sheets of polyurethane film are welded together to form the boomerang shaped two-dimensional area, which forms the upper region 62. These two sheets will form the front film 52 and middle film 54. Next, a third sheet of polyurethane (rear film 56) is welded to the middle film 54 at the point of the indentation 64, which is located approximately in the center of the rear surface of the prosthesis. This weld is formed without affecting the front film 52.

Next, all three pieces of polyurethane are welded together along the peripheral edge 51 to form the prosthesis' outer seal. Those skilled in the art will appreciate that small openings are left in the peripheral edge 51 in order to pump the silicone material into the chambers formed by the sheets of polyurethane.

After the sheets of polyurethane film are joined together to form the bag, the bag is inserted into a mold. Those skilled in the art will be familiar with suitable molds, in which a cavity forms the front surface of the prosthesis and a rear plate forms the rear surface of the prosthesis. After the bag is inserted into the mold, the front and rear chambers are filled with an appropriate two-component cross-linking silicone materials. The rear plate is then closed and the silicone materials are cured by heating the mold in an oven. Once the silicone materials are cured, the prosthesis is removed from the mold and the excess portion of the polyurethane films is trimmed around the prosthesis' peripheral edge.

The preparation of the two-component cross-linking silicone materials used in the front chamber 58 and rear chamber 60 is within the expertise of those skilled in the art. An appropriate silicone rubber material is described in detail in Patzke and Wohlfarth, "Vernetzungssyteme beim Siliconkautschuk," in CHEMIKERZEITUNG 97th year (1973) No. 4, pages 176–180, which is incorporated herein by reference. The relative stiffness of the two components may be selected as desired to provide the advantages described herein. Preferably, the silicone rubber material in the front chamber 58 has a penetration measured in a range from approximately 25.0 mm to 27.0 mm, and the silicone material in the rear chamber 60 has a penetration of approximately 10 mm. These values represent measurements with a "Precision" penetrometer using a 15 gram cone having an aluminum tip of height 0.6 inch and base diameter of 0.33 inch, and a plastic cone body extending 1.13 inches from the tip base and having a base diameter of 2.56 inches. Preferably, the thickness of the firmer rear chamber 60 is approximately 2–8% of the softer front chamber 58 at the prosthesis' thickest location (indicated by the line 74 in FIG. 5). Those skilled in the art will appreciate that these dimensions vary depending on the size of the prosthesis.

From the foregoing description, it will be appreciated that the present invention provides an attachable two-chamber breast prosthesis that ensures superior fit and transition while also providing satisfactory placement of the skin support relative to the prosthesis. By utilizing a front chamber having a periphery that is smaller than the rear chamber's, the firmer rear chamber provides enhanced stability and support sufficient to support the weight of the prosthesis when it is attached to the wearer.

What is claimed is:

1. A breast prosthesis, comprising:
   a front portion enclosed between a first film and a second film and having a first periphery; and
   a rear portion enclosed between the second film and a third film and having a second periphery;
   wherein the first periphery is smaller than the second periphery.

2. The breast prosthesis of claim 1, wherein the front portion comprises a first gel-like material and the second portion comprises a second gel-like material.

3. The breast prosthesis of claim 2, wherein the first and second gel-like materials comprise two-component cross-linked silicone materials.

4. The breast prosthesis of claim 2, wherein the first gel-like material is softer than the second gel-like material.

5. The breast prosthesis of claim 1, wherein the second and third films are bonded at a location within the second periphery.

6. The breast prosthesis of claim 1, further comprising a plurality of attachment members affixed to an exterior surface of the rear portion.

7. The breast prosthesis of claim 6, wherein one of the attachment members is a top attachment member, and wherein a top portion of the first periphery does not extend above the attachment member.

8. The breast prosthesis of claim 1, wherein a region extending from the first periphery to the second periphery has a curved shape.

9. The breast prosthesis of claim 1, wherein the first film, second film, and third film comprise polyurethane.

10. An attachable two-chamber breast prosthesis, comprising:

a front chamber formed by a first film and a second film, the front chamber being filled with a first gel-like material;

a rear chamber formed by the second film and a third film, the rear chamber being filled with a second gel-like material;

an upper region formed by joining the first film and the second film along a two dimensional area; and attachment members affixed to the exterior of the rear chamber, whereby the first and second films form a first periphery of the front chamber which is smaller than a second periphery of the rear chamber.

11. The attachable two-chamber breast prosthesis of claim 10, wherein the first gel-like material is softer than the second gel-like material.

12. The attachable two-chamber breast prosthesis of claim 10, wherein the first and second gel-like materials comprise two-component cross-linked silicone materials.

13. The attachable two-chamber breast prosthesis of claim 10, wherein the first, second, and third films comprise polyurethane.

14. The attachable two-chamber breast prosthesis of claim 10, wherein the second and third films are bonded at a location within the second periphery.

15. The attachable two-chamber breast prosthesis of claim 10, wherein one of the attachment members is a top attachment member, and wherein a top portion of the first periphery does not extend above the top attachment member.

16. A method for manufacturing a breast, comprising the steps of:

joining a two-dimensional area of a first film and a second film to form an upper region of the prosthesis;

joining the first film, the second film, and a third film along a peripheral edge to form a first chamber between the first film and a second film and a second chamber between the second film and the third film, the first chamber having a periphery that is smaller than a periphery of the second chamber;

placing the first, second, and third plastic films in a mold, the mold defining a shape of the prosthesis;

introducing a first gel-like material into the first chamber;

introducing a second gel-like material into the second chamber; and curing the first and second gel-like materials.

17. The method of claim 16, wherein the joined portions of the first and second films have a generally curved shape.

18. The method of claim 16, wherein the upper region of the prosthesis has a boomerang shape.

19. The method of claim 16, future comprising the step of bonding the second film and the third film at a location within the second periphery.

20. The method of claim 16, further comprising the step of affixing attachment members to the third film during curing.

21. The method of claim 16, wherein the first film, second film, and third film comprise polyurethane.

22. The method of claim 16, wherein the first and second gel-like materials comprise a two-component cross-linking silicone material.

23. An attachable breast prosthesis assembly comprising:
the breast prosthesis of claim 1; and
a skin support.

24. The attachable breast prosthesis assembly of claim 23, wherein the skin support further comprises an adhesive on an exterior surface of the skin support.

25. The attachable breast prosthesis assembly of claim 23, wherein the skin support further comprises attachment means on an exterior surface of the skin support.

* * * * *